United States Patent [19]
Roth et al.

[11] Patent Number: 5,902,727
[45] Date of Patent: May 11, 1999

[54] METHOD FOR LOCALIZATION AND QUANTITATION OF A SUBSTANCE IN A BIOLOGICAL SAMPLE

[75] Inventors: Kevin A. Roth; Robinna Lorenz, both of St. Louis, Mo.

[73] Assignee: Washington University, St. Louis, Mo.

[21] Appl. No.: 08/707,799

[22] Filed: Sep. 4, 1996

[51] Int. Cl.⁶ .................................................. G01N 33/53
[52] U.S. Cl. .............................. 435/7.21; 435/6; 435/7.9; 435/21; 435/28; 435/40.52; 436/518
[58] Field of Search .................................... 435/7.1, 7.21, 435/7.5, 7.9, 21, 28, 6, 40.52, 960, 973, 975; 436/518

[56] References Cited

U.S. PATENT DOCUMENTS

| | | | |
|---|---|---|---|
| 4,478,817 | 10/1984 | Campbell et al. | 435/6 |
| 4,487,830 | 12/1984 | Coates et al. | 435/7.23 |
| 5,108,896 | 4/1992 | Philo et al. | 435/7.5 |
| 5,196,306 | 3/1993 | Bobrow et al. | 435/7.9 |
| 5,487,975 | 1/1996 | Miller et al. | 435/7.5 |

OTHER PUBLICATIONS

Lansdorp et al., Immunoperoxidase procedures to detect monoclonal antibodies against cell surface antigens, quantitation of binding and staining of individual cells. Journal of Immunological Methods 39:393–405, 1980.

ICN Biomedical Catalog (ICN Biomedicals, Irvine CA, May 1992–1993, pp. 726, 727, 735, 736, 747, 1163, 1164.

Makler et al., Application of ELISA and ELADA Assay (Double Substrate Immunoassay) to Red Blood Cell Antigens, *Transfusion*; 21:303–312, 1981.

Van Leuven et al., Measurement of Immunoperoxidase Activity. A Rapid and Reproducible Immunoassay for Quantitaion of Cellular Antigens, *J. Immunol. Meth.*; 23:109–116, 1978.

*Primary Examiner*—Donna C. Wortman
*Attorney, Agent, or Firm*—Howell & Haferkamp, L.C.

[57] ABSTRACT

A method for localizing and quantitating a target substance in a biological sample is disclosed. The method utilizes an enzyme-linked probe that binds to the target substance and generates a depositable chromogenic or fluorogenic substance which detects position and a soluble chromogenic or fluorogenic substance which allows quantitation in the medium bathing the sample.

7 Claims, 8 Drawing Sheets

METHOD FOR LOCALIZATION AND QUANTITATION OF A SUBSTANCE IN A BIOLOGICAL SAMPLE

BACKGROUND OF THE INVENTION (1) Field of The Invention

This invention relates to the fields of detection of substances in biological samples and, more particularly to the localization and the quantitative analysis of substances in the same biological sample.

(2) Description of The Related Art

Diagnostic laboratories have used antibodies, lectins, nucleotide probes and the like for many years to localize target substances in cells and tissues. The binding of such probes to the target substance is typically detected microscopically by the use of direct labeled probes such as fluorophores, enzyme conjugates, gold particles and the like or by conjugated "secondary" probes that recognize the "primary" probe. This basic protocol continues to be used in numerous clinical and research laboratories. Recent advances in detection systems have improved the sensitivity and resolution of the probe localization and include such methods as immunogold with silver intensification, peroxidase-anti-peroxidase, avidin-biotin complex, and tyramide signal amplification. Although these methods provide excellent spatial resolution of antigen distribution, they do not provide any direct quantitative information about the target substance. One method for obtaining such quantitative information has been by the use of image analysis, however, this approach requires a significant amount of time and expense.

Numerous techniques exist for the quantitation of substances in cells and tissues including Western, Southern and Northern blots, radioimmunoassays, ELISA assays and dot blot assays. While these techniques can provide useful quantitative information, they typically provide no information at all about the localization of the target substance within the cells or tissues. Furthermore, the methods often require tissue extraction and/or disruption which precludes localization of the target substance. Nevertheless, it is often essential in the clinical laboratory setting to obtain information on both the distribution of a substance within a cell or tissue as well as the quantitative amount of the substance present in the tissue.

Although some approaches have reported on attempts to obtain information in addition to the histochemical localization or in addition to the quantitative amount of the substance present, few reports have been published on approaches other than image analysis achieving both localization and quantitation of a substance in a biological sample. In some studies, the quantitation of a substance present in a cell suspension has been coupled with a determination of the number of positive cells, i.e. a cell count (for example see, Makler et al, *Transfusion*21:303–312, 1981). Such studies, however, provide no information on the localization of a target substance within the cell suspension.

In another report, quantitative detection has been performed that uses an immunohistochemical technique used earlier for antigen localization. (Leuven et al., *J Immunol Meth*23:109–116, 1978). The method reported in this study, however, disrupted the cells prior to quantitative determination of the antigen. Thus, in both the Leuven et al. and Makler et al. methods, to perform both quantitation and localization, duplicate preparations were indicated to be required.

Another group reported on an assay system in which both quantitation and localization was determined in the same sample (U.S. Pat. No. 4,487,830). This method utilized a fluorescent antibody to detect the localization of the target substance and an enzyme-linked antibody to quantitate the presence of the target substance or, alternatively, a fluorescent antibody conjugated to an enzyme. However, fluorescent antibodies provide minimal signal amplification and require microscopes with epifluorescence attachments for visualization of signal which are not routinely available in clinical laboratories.

In another report a probe labeled with a chemiluminescent or bioluminescent substance was used that reacted with other substrate molecules to produce light (U.S. Pat. No. 4,478,817). Localization was by visual inspection and quantitation could be obtained from the total of light emitted from the sample using, for example a photo multiplier tube. Such quantitation is difficult to perform and time consuming and requires equipment not routinely found in clinical laboratories. Furthermore, none of the above cited references describe procedures for multi-probe detection. Thus, variance in tissue or cell amounts can not be determined on single samples using these techniques.

Thus it would be desirable to have a simple and inexpensive method for detecting both the localization and quantitation of a substance in cells or tissues that can be used in virtually any clinical laboratory and that does not require fluorescent microscopy or image analysis.

BRIEF DESCRIPTION OF THE INVENTION

Accordingly, the inventors herein have succeeded in devising a novel method for localizing and quantitating a target substance in a biological sample in a bathing medium. The method comprises contacting the sample with a probe which binds to the target substance wherein the bound probe is linked to an enzyme. The enzyme produces, from a first substrate, a first product which deposits substantially at the location of the target substance. The enzyme also forms, from a second substrate, a second product which remains in the bathing medium and can be detected upon illumination of the bathing medium. The second product is present in the bathing medium in an amount that is quantitatively related to the amount of target substance in the sample. Thus, by measuring the amount of product in the bathing medium, the amount of target substance in the sample can be determined.

A variety of different probes can be used in the method including an antibody, an avidin compound, a lectin, a receptor ligand and a nucleotide probe. Furthermore, the probe can be linked to any of a number of enzymes including alkaline phosphatase, horseradish peroxidase, β-galactosidase, glucose oxidase, α-amylase, β-glucuronidase, neomycin phosphotransferase, chloramphenicol acetyl transferase, and β-lactamase. Moreover, the enzyme can act upon any of a number of substrates to form a product that deposits for localization determination or a product that remains in the bathing medium for quantitative analysis.

The method can also be used for localizing and quantitating at least two target substances by using an enzyme-linked probe for each target substance detected along with substrates that form distinct deposited and solution phase products for each target substance.

In another embodiment a kit is provided for localizing and quantitating a target substance in a biological sample in a bathing medium. The kit is comprised of a probe which binds to the target substance or a binder which associates with or binds to a probe bound to the target substance. The probe is linked to an enzyme which produces from a first substrate a first product which deposits substantially at the target substance location. The first product can be detected upon illumination of the sample. The enzyme also forms a second product which can be detected upon illumination of the bathing medium in an amount that is dependent upon the amount of target substance in the sample. A variety of probes can be used including an antibody, an avidin compound, a lectin, a receptor ligand and a nucleotide probe. Furthermore, a number of enzymes can be used including alkaline phosphatase, horseradish peroxidase, β-galactosidase, glucose oxidase, α-amylase, β-glucuronidase, chloramphenicol acetyl transferase, neomycin phosphotransferase, and β-lactamase. Moreover, a variety of substrates can be used to produce any of a number of depositable products and solution phase products.

The kit can also be used for localizing and quantitating at least two target substances by using an enzyme-linked probe for each target substance detected along with appropriate substrates that form distinct deposited and solution phase products for each target substance.

Among the several advantages that are achieved by the present invention, therefore, may be noted the provision of an inexpensive, rapid and simple-to-perform method for detecting both the location and quantitative amount of a target substance in a biological sample; the provision of a method for both localizing and quantitating a target substance which can be routinely used in most clinical laboratories and that does not require complex and expensive instrumentation; and the provision of a kit that can be used to perform such a method.

DETAILED DESCRIPTION OF THE INVENTION

Figure 1:
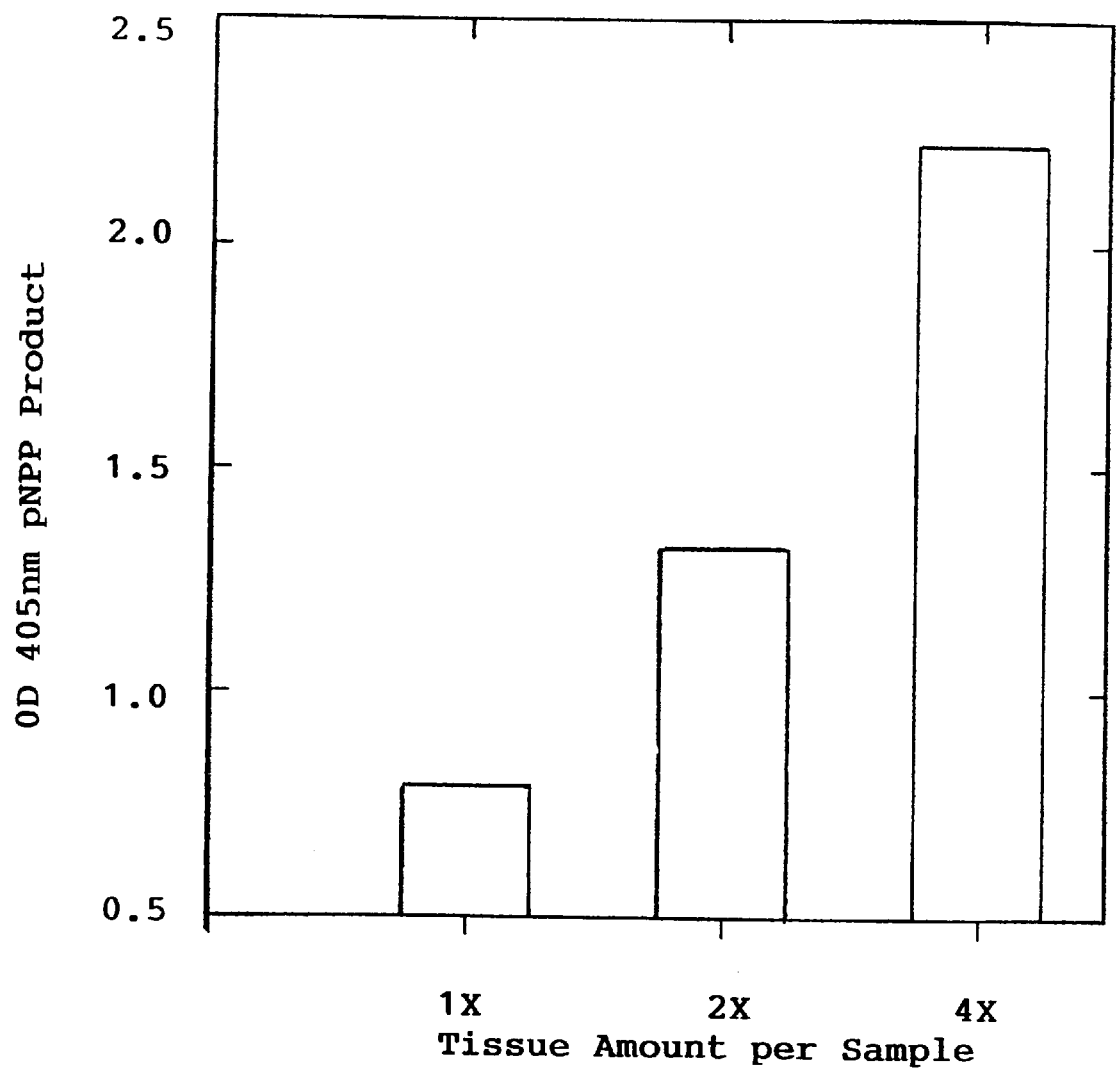
FIG. 1 illustrates the direct relationship between the amount of chromogen detected in solution phase and the amount of the target substance present within the sample.

In accordance with the present invention, it has been discovered that the quantitation and localization of a substance in a single biological sample can be accomplished rapidly and without the use of radioisotopic, fluorescent or chemiluminescent detection systems and without the use of image analysis equipment. The method uses a probe which binds the target substance wherein the probe is linked to an enzyme capable of producing detectable chromogenic or fluorgenic substances from substrates present in the medium bathing the sample. The enzyme produces one chromogenic or fluorgenic substance which deposits at the site of the target substance and a second chromogenic or fluorgenic substance which remains in the solution phase for detection by quantitative analytical methods.

The sample can be any of a variety of biological samples such as cell cultures, tissue specimens, serum samples suspected of containing autoimmune or immune antibodies and the like. The sample can be obtained from a patient which can include both human and veterinarian patients or the sample can be from a cultured cell line or tissue. Preparation of the sample can be by any of a number of routinely used methods for immobilization on to the surface of a support substrate such as a microscope slide, microtiter dish well, membrane, petri plate, or the like. The target substance thereby becomes fixed to the support substrate. Any of a number of methods can be used in fixing the sample to the support substrate. The types of samples prepared can include paraffin embedded tissues, frozen tissue sections, cells in tissue culture wells, or another cell sample in which the cells are fixed or bound to the supporting substrate.

The target substance in the biological sample can be any of a number of intracellular or extracellular substances such as, for example, DNA, RNA, antigen, antibody, receptor, hormone or other receptor ligand, lipid, phospholipid, glycolipid, glycoprotein, carbohydrate substance, or the like. The target substance can be in solution phase prior to preparation so long as it is fixed on a solid substrate after preparation in such a manner that the target substance can be localized and quantitated. By localization it is meant that the position of the target substance is determined with respect to the tissue, cell or subcellular components of the sample. Such determination might be referenced within a cell or with respect to a cell, such as where the target substance can be either intracellular or extracellular, or the determination may be referenced within a tissue or tissues such as where the location of cells producing a particular substance is being determined.

The probe can be any of a number of substances capable of binding to and allowing detection of the target substance. For example, the probe can be an antibody either monoclonal or polyclonal, where the target substance is an antigen; an avidin such as streptavidin where the target substance is biotin or a biotinylated protein; a lectin where the target substance is a carbohydrate; a sense or antisense nucleotide capable of hybridizing with a DNA or RNA target substance; a protein or peptidomimetic ligand which is capable of binding to a receptor; or any substance capable of binding to the target substance being detected.

A probe which is bound to a target substance can also be bound by additional probes. The binding of such a second probe to the first probe can serve to link the first or subsequent probe to the enzyme which allows detection of the location and quantitation of the bound probe and, hence, the location and quantitation of the target substance.

Thus the probe is linked or conjugated to an enzyme and such linkage can be direct as where the probe is an antibody conjugated to the enzyme or indirect where the enzyme is conjugated to an antibody which then binds to the antibody that reacts with the target substance. Thus, in the indirect embodiment, the enzyme is linked to a binder which can be virtually any substance that will bind to, i.e. associate with, the probe. Where the probe is a polynucleotide, it can be conjugated to digoxygenin, biotin or other molecule that is then bound by another substance to which is conjugated the enzyme. Hence, two or more binding substances can be conjugated or linked to each other, only one of which need be covalently linked to the enzyme and another of which can serve as the probe for binding to the target substance.

Enzymes useful in the present invention are preferably readily available, stable at room temperature, and capable of stably maintaining its enzymatic activity after reaction with the one or more chromogenic or fluorgenic substances used in the detection assay. Some such enzymes usable in the present invention include calf intestine alkaline phosphatase, horseradish peroxidase, β-galactosidase, glucose oxidase, α-amylase, β-glucuronidase, neomycin phosphotransferase, chloramphenicol acetyl transferase, β-lactamase and the like.

The enzyme or enzymes act upon substrates in the medium bathing the biological sample to produce both a soluble and a deposited reaction product which typically deposits by virtue of its being insoluble in the bathing medium. It is preferred that both the soluble and deposited reaction products which are chromogenic or fluorgenic substances remain stable in their detectable chromogenic or fluorgenic form so that both localization and quantitation can be determined for an extended period of time. This is particularly preferred for the histochemical localization aspect of the present invention in which it is sometimes desirable to reexamine the target substance localization or use the sample in reference comparisons such as, for example, in monitoring the course of changes in a disease process.

The soluble and insoluble reaction products can be produced from substrates that are different. Particular substrates and products are selected to correspond to the particular enzyme. Thus, for example where the enzyme is alkaline phosphatase (AP), the deposited product can be produced from a substrate such as 5-bromo-4-chloro-3-indolyl phosphate/nitro blue tetrazolium (BCIP/NBT), New Fuchsin, Fast Blue/Naphtol or Fast Red/Naphthol and the soluble product can be produced from a substrate such as Fast Red/Naphtol or p-nitrophenyl phosphate (pNPP). Where the enzyme is horseradish peroxidase (HRP), the deposited product can be produced from a substrate such as o-phenylene diamine dihydrochloride (OPD), p-phenylene diamine dihydrochloride/pyro catechol mixture (pPD/PC), amino ethylcarbazole, chloro-naphthol, or diaminobenzidine tetrachloride/cobalt chloride and nickel chloride mixture (DAB/metal), and the soluble product can be produced from a substrate such as OPD, pPD/PC, or tetramethyl benzidine dihydrochloride (TMB).

Soluble reaction products are generally produced without a substantial decrease in enzyme activity. Insoluble reaction products often produce a decrease in enzyme activity. It would be desirable, therefore, to utilize insoluble reaction products that do not substantially reduce enzyme activity. Preferably, the enzyme activity is decreased by production of either soluble or insoluble products by not more than 90%, more preferably by not more than 50%, still more preferably by not more than 20%, and most preferably by not more than 10% or less. In an alternative preferred embodiment, the soluble product for quantitative determination of the presence of the target substance can be formed first, followed by formation of an insoluble, depositable product that more typically causes a decrease in enzyme activity.

In some instances, more than one product is formed by the enzyme from the same substrate or, in other instances, the product can be partially soluble and partially insoluble. Under these circumstances a single substrate can be used to detect both the localization and quantitation of the target substance.

The products produced by the enzyme are chromogenic or fluorgenic substances. As used herein, the terms chromogenic or fluorgenic substance are intended to mean a substance which upon illumination produces a detectable electromagnetic radiation. Chromogenic substances are substances containing chromophores and fluorgenic substances are containing fluorophores. Alternatively, a target substance can be localized upon precipitation of an insoluble metal salt. The soluble product or chromogenic or fluorgenic substance is detected in the solution phase. The solution phase product can absorb light at a preferred wavelength depending on the particular chromogenic or fluorgenic substance. One skilled in the art can readily ascertain the preferred wavelength for a particular chromogenic or fluorgenic substance.

The measurement of light absorbance for the solution phase containing the dissolved chromogenic or fluorgenic substance can be by any of a number of methods such as, for example, by use of a multiple wavelength spectrophotometer.

The deposited chromogenic or fluorgenic substance becomes concentrated in the solid phase at or near the site of the probe binding and, hence, at the site of the target substance. The deposited solid phase chromogenic or fluorgenic substance can provide a localized color and contrast to a sample being analyzed and thereby identify the position of the target substance within the sample when the solid phase sample is illuminated with light under a microscope.

Thus, the localization of the target substance is accomplished by generation of a deposited chromogenic or fluorgenic substance which deposits in the solid phase substantially at the target substance location marked by the binding site of the probe to the target substance. The closeness to the target substance required for localization of that target substance will depend upon the requirements of the particular assay. For localization of a target substance on or within a cell, substantially at the target substance location is intended to mean that the deposit site is preferably within about 2 microns, and more preferably within about 0.5 micron, and most preferably within about 0.1 micron of the target substance location. Where the localization of a target substance within a tissue is to be determined, the deposit site is preferably within about 5 microns, more preferably within about 2 microns, and most preferably within about 0.5 microns from the target substance location.

The sample is bathed in a medium which is a solution in contact with the fixed sample. The bathing medium is preferably a buffered aqueous solution which can contain any of a number of salts compatible with the probe and enzyme as well as the sample and target substance. In addition, bathing medium can in some cases contain detergents to facilitate dispersion of insoluble probe-enzyme conjugates. The probe-enzyme conjugate and substrate are maintained in solution, suspension or dispersion within the bathing medium which makes up the liquid phase of the detection system. If the sample is on a non-enclosed surface such as a glass slide, a barrier can be formed around the tissue with water resistant material and the solution phase can be removed to a separate container for quantitation.

It is also possible to increase the sensitivity of detection by the probe by incorporating into the method standard amplification procedures that can increase the number of signal molecules which are near to the site of the probe bound to the target substance. For example, the secondary binding of polyclonal antibody conjugated to enzyme to a monoclonal antibody bound to the target substance greatly increases the number of enzyme molecules present at or near the monoclonal probe binding site, thus increasing the amount of chromogenic or fluorgenic substance produced.

One particularly useful method for signal amplification is described in U.S. Pat. No. 5,196,306 and the corresponding commercial kit form known as the biotin tyramide signal amplification (TSA, New England Nuclear Life Science Products, Boston, Mass.) method. The method utilizes an enzyme-linked antibody that binds to a target substance. The enzyme then reacts with an added first substrate in solution to produce a reactive biotin-linked product which deposits on the sample near the target substance. Another solution is then applied which contains enzyme-conjugated streptavidin which binds to the biotinylated product to produce an amplification of enzyme activity in the local area defined by the initial antibody-enzyme conjugate. This method along with other methods capable of amplification of enzyme activity linked to the probe can be used with the method in this invention, for example, indirect detection with fluorescent streptavidin or gold labeled streptavidin with silver intensification.

The quantitation aspect of the present invention relies on the solution phase generation of an enzyme reaction product which proceeds to an end point determined by the substrate or the product or, alternatively, the reaction can be terminated by removal of the solution phase from the enzyme or by addition of acids, bases, reducing agents, chaotropic agents or the like to a sample of the solution phase first removed from the enzyme. A chromogenic or fluorgenic substance is thereby produced which can be detected spectrophotometrically. If one of the several terminating agents is used, it may be preferred to perform the localization method first where it is possible that the enzyme activity might be diminished after treating with a terminating agent.

The quantitative determination preferably utilizes appropriate controls such as samples which do not react substrate with enzyme by virtue of either or both of the substrate and enzyme not being present. Other controls such as omission of probe or pre-absorption of probe with excess target substance prior to sample incubation can also be performed. In addition, positive controls will consist of addition of known amounts of enzyme and substrate such that a standard curve for enzyme concentration can be constructed for comparison with an unknown sample to which enzyme linked probe is added.

The sample may be treated prior to addition of the probe and enzyme to remove or destroy endogenous enzyme activity which could interfere with the detection. For example, many cells or tissue specimens may normally contain endogenous phosphatase or peroxidase enzymes which can also act upon the substrate. Such treatment methods include chemical treatment or brief boiling. In addition, surface sites unrelated to the target substance can sometimes also bind the probe nonspecifically. To reduce this nonspecific binding, the sample can be coated with a solution which contains a reagent which binds to and masks or generally blocks such nonspecific binding sites. Some such masking or blocking agents include gelatin, bovine serum albumin, powdered milk and some detergents.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the relationship between the amount of chromogen detected in solution phase measured by optical density and the amount of target substance present in a sample.

All reagents were obtained from Sigma Chemical Company, St. Louis, Mo. and all incubations were at room temperature, unless otherwise specified. Mouse brain tissue was embedded in paraffin and the binding to the tissue was determined for a wheat germ agglutinin-alkaline phosphatase conjugated lectin probe (WGA-AP, EY Laboratories). Wheat germ agglutinin binds to N-acetylglucosamine sugar residues present in abundance on the surface of most mammalian cell types.

Varying amounts of tissue were used in each test assay. For example, a sample of tissue was fixed to one microscope slide, approximately twice as much tissue was fixed to another, and approximately four times as much tissue was fixed to still another slide. Each sample was tested in duplicate.

After fixing the specimens the paraffin was removed and the endogenous alkaline phosphatase was destroyed by boiling in water for five minutes in a microwave oven. After washing the specimens sequentially in water, PBS (0.1M phosphate buffered saline, pH 7.2) and PBS-BB (PBS with 1% bovine serum albumin, 0.2% powdered milk, and 0.3% TRITON X–100detergent ), the WGA-AP enzyme-probe conjugate (200 $\mu$l of a 1:200 dilution of a 1 $\mu$g/ml WGA-AP stock in PBS-BB) was applied to each specimen and incubated overnight at 4° C. Control samples for each tissue amount were also treated with PBS-BB without WGA-AP and were also incubated at 4° C. overnight. Each specimen was washed three times for five minute each time with Tris (20 mM, pH 7.5), and overlaid with 200 $\mu$l of a solution containing pNPP (0.2M Tris pH 9.9, 1 mg/ml pNPP). Prior to pNPP addition, a "barrier" was formed around tissue sections on microscope slides by application of a water resistant material using a grease pen or fingernail polish to isolate the tissue. The pNPP reaction was allowed to react for ten minutes, at which point 100 $\mu$l was removed to a well in a microtiter plate containing 25 $\mu$l 3N NaOH to terminate any further phosphatase activity. The quantity of enzyme present in each sample was determined by measuring the absorbance of each sample removed and stopped with NaOH at 405 nm using a microtiterplate spectrophotometer. Absorbance values were recorded for each sample specimen, and paired specimen values were averaged and plotted against tissue amount.

Each specimen was then washed three times with Tris buffer and treated for ten minutes with 200 µl of a solution containing BCIP/NPT (0.1M Tris pH 9.4, 0.15 mg/ml BCIP, 0.3 mg/ml NBT, 0.005M $MgCl_2$ (pH >7.5). The BCIP/NBT solution was washed from each specimen with Tris and the sections were boiled in water for two minutes. Boiling changes the color of the deposited BCIP/NBT reaction product from brown/purple to blue. Sections were examined under a light microscope for the presence and intensity of blue color on the cells present in each sample.

The amount of residual endogenous phosphatase activity present in each control specimen after microwave boiling was found to be negligible and no increase in phosphatase activity was seen as the amount of sample increased from 1× to 2× to 4×. Localization of the precipitated BCIP/NBT was identical in all of the WGA-AP treated brain specimens and was found diffusely throughout the neuropil. No staining was detected in the absence of WGA-AP (Data not shown). When the optical density measurement for the WGA-AP samples were corrected for control absorbance, the amount of binding of the probe-conjugate to the samples showed a progressive increase that is directly proportional to the amount of tissue present in the sample (Table 1).

TABLE 1

| Tissue Amount | WGA-AP ($OD_{405}$) | Corrected WGA-AP $OD_{405}$ (-Control $OD_{405}$) | Mean Corrected WGA-AP |
|---|---|---|---|
| 1X | 0.790 | 0.661 | 0.790 |
| 1X | 1.048 | 0.919 | |
| 2X | 1.212 | 1.079 | 1.324 |
| 2X | 1.702 | 1.569 | |
| 4X | 2.428 | 2.293 | 2.223 |
| 4X | 2.228 | 2.153 | |

FIG. 1 further illustrates the direct relationship between the amount of tissue present in a sample and the amount of product produced. Thus, there is a linear relationship between the amount of probe which binds to a target substance in a sample and the amount of tissue or concentration of cells in that sample.

EXAMPLE 2

This example illustrates the relationship between reaction time and amount of chromogen detected measured by optical density.

Duplicate sections from specimens of mouse brain were prepared as in Example 1 except that each pair of samples was reacted with substrate for different times and the optical density measured. This allowed the determination of the relationship between the amount of chromogen produced and reaction time. Duplicate control sections received PBS-BB without WGA-AP.

At each time point, 100 µl of solution was removed from a given sample and placed into a microtiter well containing 25 µl 3N NaOH which terminated the enzyme reaction. Absorbance was then measured at 405 nM.

Each specimen was then washed and reacted with BCIP/NBT as in Example 1 and microscopically observed for the presence and intensity of color deposit.

The absorbance of each solution phase sample increased with increasing reaction times (Table 2). Negligible absorbance was observed in the PBS-BB control sections. The blue color deposited onto each sample at the end of ten minutes with BCIP/NBT appeared to be identical among the WGA-AP samples upon microscopic examination as would be expected since the deposited chromogen reaction was performed for an identical time. No staining was observed in the PBS-BB control sample.

TABLE 2

| Reaction Time (minutes) | $OD_{405}$ | Average $OD_{405}$ | Corrected $OD_{405}$ |
|---|---|---|---|
| 0 | 0.132 | 0.112 | 0 |
| 0 | 0.091 | | |
| 2 | 0.311 | 0.424 | 0.312 |
| 2 | 0.537 | | |
| 4 | 0.421 | 0.470 | 0.358 |
| 4 | 0.519 | | |
| 8 | 1.094 | 1.123 | 1.011 |
| 8 | 1.152 | | |
| 16 | 1.825 | 2.150 | 2.038 |
| 16 | 2.475 | | |
| PBS-BB/16 | 0.123 | 0.117 | 0.005 |
| PBS-BB/16 | 0.110 | | |

Figure 2:
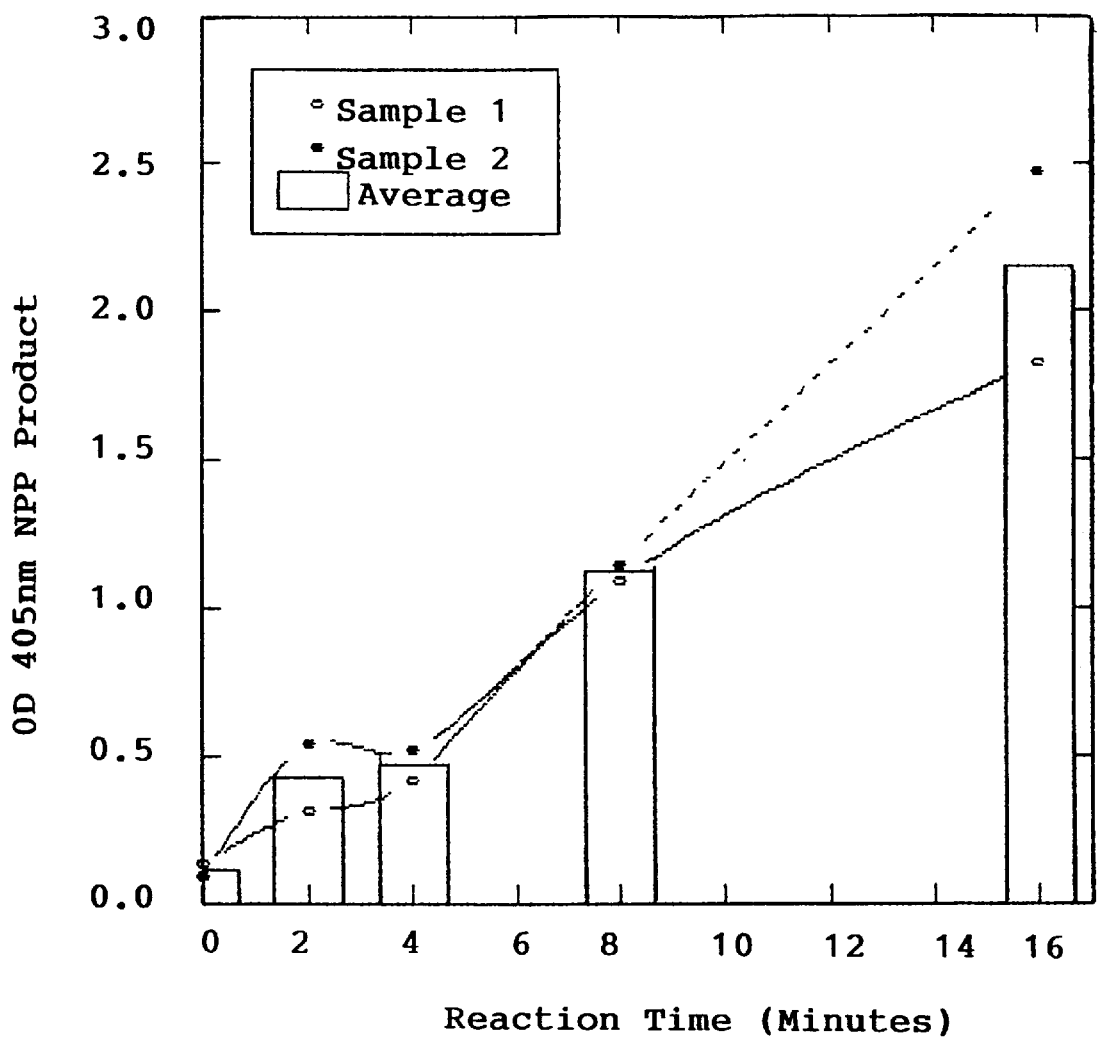
FIG. 2 illustrates the relationship between the amount of chromogen detected in solution phase and the amount of time the solution phase remains in contact with the sample.

FIG. 2 illustrates the data in Table 2 showing a direct nearly linear relationship between the amount of chromogen detected and the length of time the reaction proceed.

EXAMPLE 3

This example illustrates the percent loss in enzyme activity upon sequential reactions of the enzyme bound to the sample with substrate in the medium. Sections of paraformaldehyde fixed mouse brain were prepared in duplicate, treated with WGA-AP probe at in PBS-BB, reacted with pNPP substrate, 1:100 dilution in PBS-BB, reacted with pNPP substrate, and the absorbance was measured at 405 nM as in Example 1. Each sample was then washed three times with Tris buffer, and subjected to a second reaction with a fresh solution of pNPP substrate and measured at 405 nm. $A_{405}$ values obtained for each pNPP reaction were averaged.

The sample was then washed three times with Tris buffer and reacted for ten minutes with a standard BCIP/NBT solution followed by washing with water, brief boiling, and observation under a light microscope.

The amount of chromogen measured in the second reaction was decreased compared to that measured in the second reaction with a mean decrease of 15% ±2% for both samples. Microscopic observation of the solid phase chromogen showed intense blue color as was seen in samples from Examples 1 and 2, indicating that localization of the chromogen is not detectably altered by prior repeated solution phase reaction.

EXAMPLE 4

This example illustrates the sequential visual and quantitative determination of apoptotic cells using the TUNEL assay (TdT-mediated dUTP Nick End Labeling assay).

Tissue sections from a young adult mouse thymus which has a moderate level of cellular apoptosis were prepared as in Example 1. Cells undergoing apoptosis were labeled using terminal deoxynucleotidyl transferase (TdT) with digoxygenin-dUTP (dig-dUTP) (Both products of Boehringer Mannheim Biochemicals (BMB), Indianapolis, Ind.). Apoptotic cells contain DNA which has become damaged and therefore has exposed free terminal nucleotidyl residues in the nucleus. As a result TdT is able to incorporate dig-dUTP onto these DNA ends in these cells and not in normal cells. Specimens were deparaffinized, washed in water, and washed again in PBS buffer. Sections were then reacted with TdT (0.5 µl of 25 U/100 µl enzyme) in 30 mM Trizma base, pH 7.2, 140 mM sodium cacodylate, 1.0 mM cobalt chloride, and 0.25 µl of 0.25 nmol/100 µl of dig-dUTP for sixty minutes at 37° C. The reaction was stopped by washing in 300 mM NaCl, 30 mM sodium citrate. Specimens were then washed in water and blocked in PBS-BB for thirty minutes. A PBS-BB solution containing horseradish peroxidase labeled anti-digoxygenin monoclonal antibody (Boehringer Mannheim Biochemicals) was incubated with the tissue specimens overnight at 4° C. Specimens were then subjected to three five minute washes in Tris buffer, and the TSA technique was performed according to the manufacturer's protocol. HRP-streptavidin was used to bind to the deposited biotin tyramide, washed three times for five minutes each in Tris buffer, and specimens were then incubated for five minutes with 200 µl TMB (0.1 mg/ml TMB in phosphate citrate buffer with sodium perborate pH 5.0).

A 100 µl sample of solution was removed from each specimen and placed into a microtiter plate well which contained 25 µl of 2M $H_2SO_4$ and analyzed at 450 nM to quantitate the amount of reaction product produced from each tissue specimen. Each specimen was subjected to three five minute washes with Tris buffer, covered with 200 µl of a standard DAB/metal solution (Pierce) for 5 minutes, washed again, and visually examined under a light microscope for the presence and location of dark brown apoptotic cells. The specimens were then photographed. One specimen that was not reacted with TdT served as a negative control.

Figure 3A:
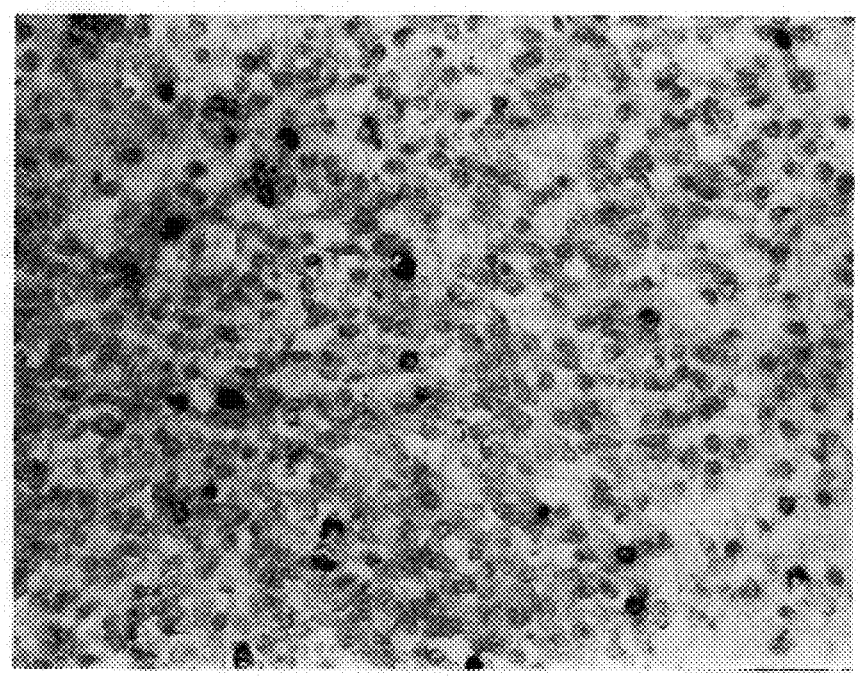
FIGS. 3A and 3B illustrates the apoptotic assay of thymus tissue sections in (A) cells labeled with digoxygenin-dUTP and probed with horseradish peroxidase conjugated anti-digoxygenin antibody and (B) cells unlabeled and probed with horseradish peroxidase conjugated anti-digoxygenin antibody.
Figure 3B:
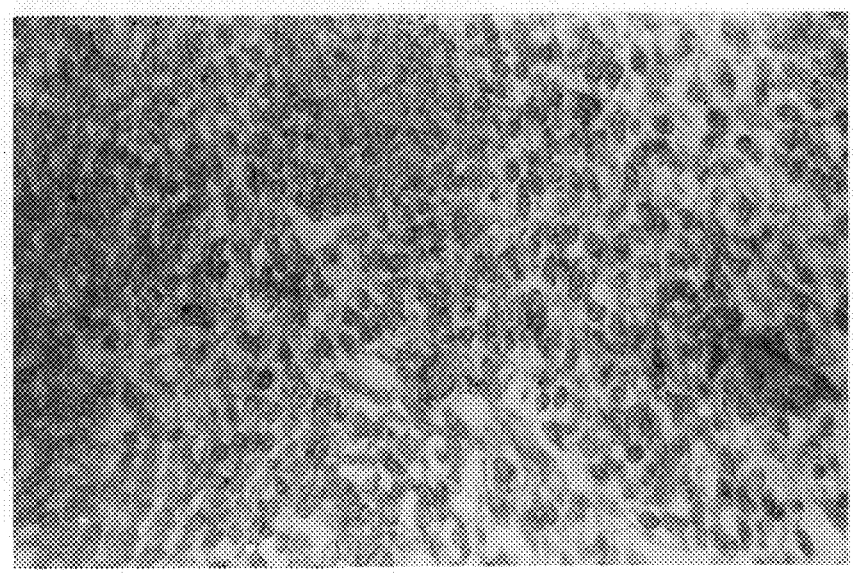
Figure 4A:
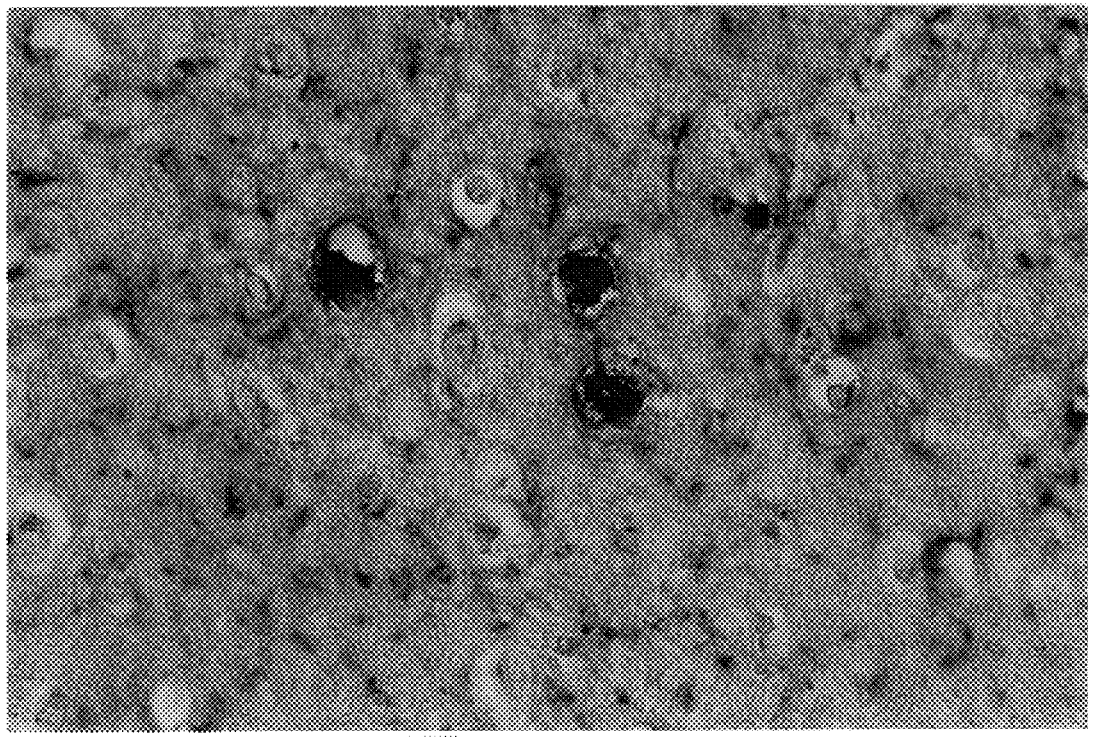
FIGS. 4A, 4B, 4C and 4D illustrates Alzheimer's assay of patient tissue sections probed with (A) mouse anti-PHF/tau antibody amplified by TSA and bound by alkaline phosphatase conjugated streptavidin reacted with BCIP/NBT and boiled in water to produce a blue color (40X); (B) rabbit anti-Gfap antibody bound by alkaline phosphatase conjugated goat anti-rabbit antibody reacted with BCIP/NBT to produce a brown/purple deposit (40X); (C) mouse anti-PHF/tau antibody amplified by TSA and bound by alkaline phosphatase conjugated streptavidin reacted with BCIP/NBT and boiled in water to produce a blue deposit, followed by rabbit anti-Gfap antibody bound by alkaline phosphatase conjugated goat anti-rabbit antibody reacted with BCIP/NBT to produce a brown deposit (10X); and (D) mouse anti-PHF/tau antibody amplified by TSA and bound by alkaline phosphatase conjugated streptavidin reacted with BCIP/NBT and boiled in water to produce a blue deposit, followed by rabbit anti-Gfap antibody bound by alkaline phosphatase conjugated goat anti-rabbit antibody reacted with BCIP/NBT to produce a brown deposit (40X)
Figure 4B:
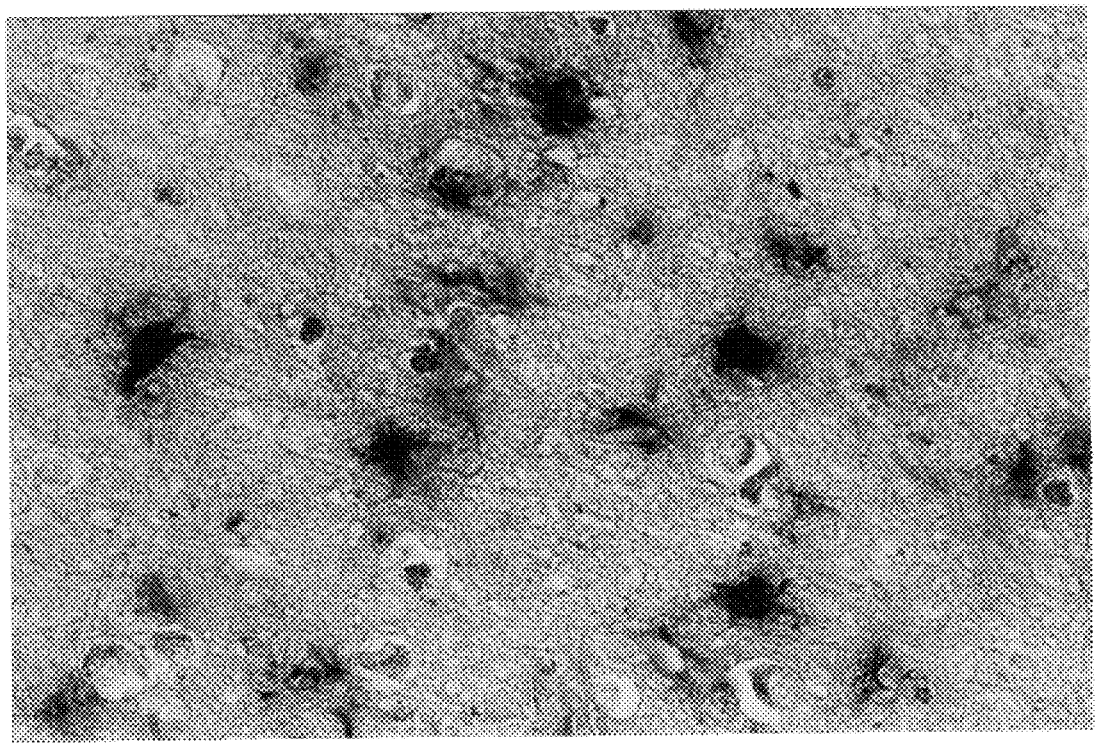
Figure 4C:
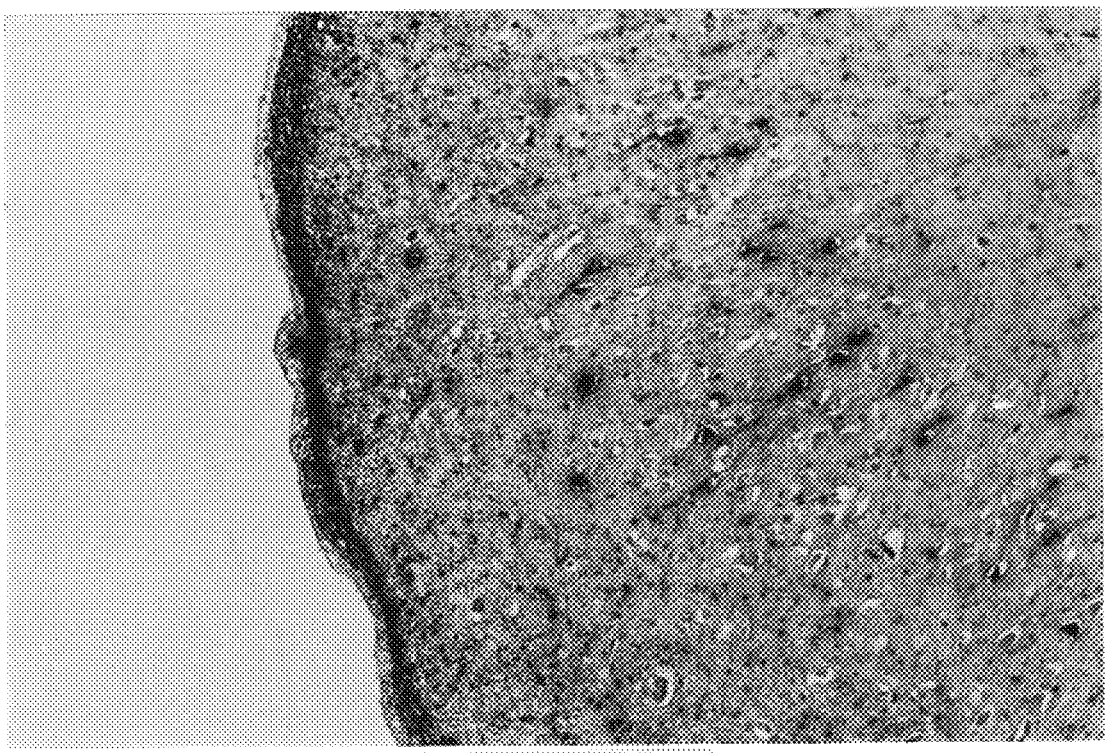
Figure 4D:
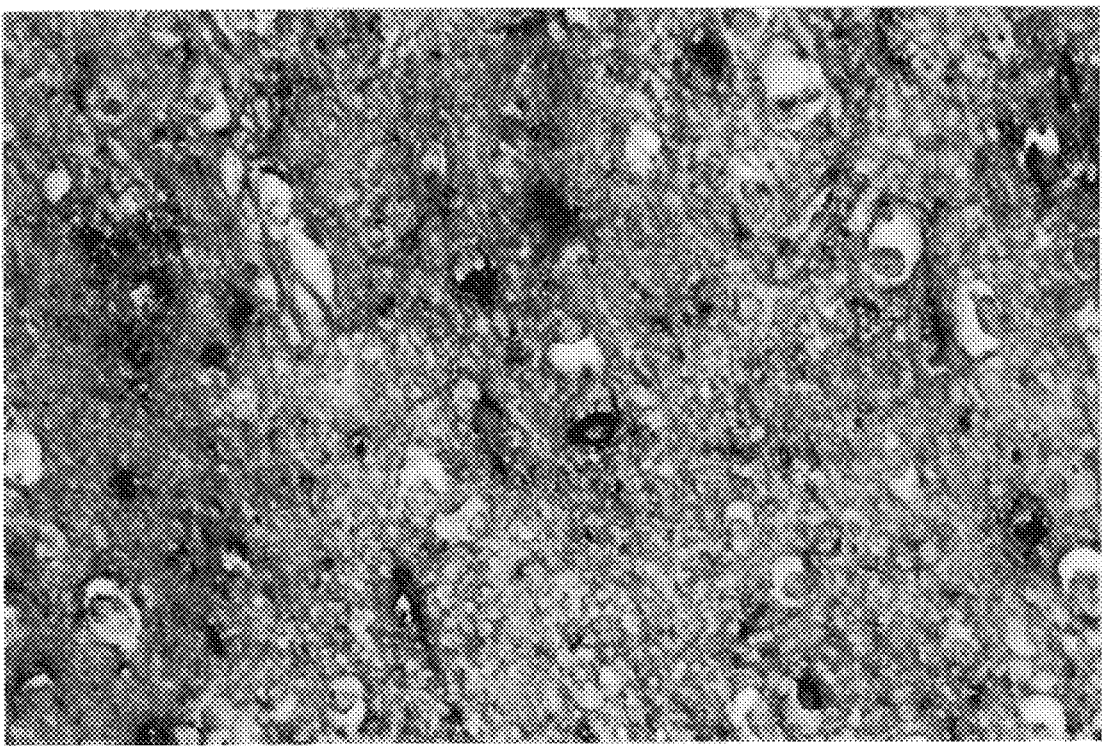

The sample treated with TdT, anti-dig antibody, and HRP conjugated streptavidin showed cells with darkly stained nuclei which represent apoptotic cells in the sample (FIG. 3a). In contrast, no darkened nuclei were observed in the sample not treated with TdT (FIG. 3b). The quantitative measurement from the TdT treated sample gave an optical density at 450 nM of 0.625 compared to 0.312 for the untreated sample. Thus the solution phase detection of apoptotic mass showed the detection of the amount of apoptotic mass in the specimen.

EXAMPLE 5

This example illustrates the sequential quantitation and localization of PHF/tau and glial fibrillary acidic protein (Gfap) in single specimens.

Patients with Alzheimer's disease have increased amounts of PHF/tau deposited in their brains. They may also have loss of neurons and an increase in reactive astrocytes that label with anti-Gfap antibodies. In contrast, patients with other nervous system diseases may have increased amounts of Gfap but do not have increased PHF/tau reactivity.

Human brain sections from five patients, two with Alzheimer's disease and three without, were prepared as in Example 1. The samples had varying degrees of reactive astrocytosis as evidenced by neuropathologic examination. Sections were treated with 0.3% $H_2O_2$ in methanol for thirty minutes to reduce or eliminate endogenous peroxidase activity. Three separate section samples from each of the five human brains were used for each probe: two treated with a single probe and the third treated sequentially with the two probes.

All three tissue specimens from each patient's brain were blocked in PBS-BB for fifteen minutes. Two sections were covered with 10 µl of a 1:5000 dilution of mouse anti-PHF/tau antibody (Innogenetics) in PBS-BB for one hour and a third received just PBS-BB. After washing thoroughly three times for five minutes each time in PBS, each sample was covered in a 1:1000 dilution of biotin conjugated donkey anti-mouse antibody (Jackson Immuno-Research Laboratories) in PBS-BB for one hour, and followed with one wash in PBS and two in Tris as above. A 1:500 dilution of horseradish peroxidase conjugated streptavidin (HRP-Strep) in TNB (Tris buffer containing 0.5% Dupont Blocking Reagent supplied with TSA Kit) was placed onto these specimens for thirty minutes, then washed three times as before in Tris buffer. A 1:100 dilution of Biotin Tyramide (NEN Life Sciences, Dupont) in 1× amplification buffer (supplied with TSA Kit) was reacted with each of these samples, which provides a substrate catalyzed by HRP to a reactive product which deposits onto and binds to molecules on the surface of the specimen, providing an increased local concentration of biotin linked substrate for subsequent streptavidin-enzyme conjugate to bind to. The samples were then washed again in Tris, and an alkaline phosphatase conjugated streptavidin (AP-Strep) (Jackson ImmunoResearch Laboratories) diluted 1:1000 in TNB was placed onto each sample for thirty minutes. This was then removed by washing three times with Tris buffer, followed by overlaying with 300 µl of pNPP solution for six minutes. 100 µl was removed from each sample and placed into a microtiter dish well containing 25 µl of 3N NaOH to terminate any enzyme reaction, and each sample was analyzed spectrophotometrically at 405 nm.

The samples were then subjected to three washes with Tris buffer, and overlaid with a BCIP/NBT solution for ten minutes and washed thoroughly in water. The sections were then boiled in water for two minutes in a microwave oven to physically convert the deposited brown/purple BCIP/NBT chromogenic substance to blue, and to destroy the horseradish peroxidase and alkaline phosphatase enzyme activities used to detect PHF/tau probe binding. One sample was analyzed under a light microscope to localize positions of probe binding to concentrated areas of PHF/tau binding. The other sample was analyzed further using anti-Gfap antibody.

This section along with one additional brain section which had been subjected to all conditions up to the blocking buffer step were treated as follows. The two sections were treated first with a 1:2000 dilution of rabbit anti-Gfap antibody (DAKO) diluted into PBS-BB. This was allowed to react with each sample overnight at 4° C. After washing off excess probe, each sample was overlaid with an alkaline phosphatase conjugated goat anti-rabbit polyclonal antibody (Jackson ImmunoResearch Laboratories) diluted 1:50 in PBS-BB for one hour. Excess secondary antibody was washed off as before and the samples were reacted with 300 µl of a standard pNPP solution for 10 minutes, a 100 µl sample was removed as in example 1 and quantitated at 405 nm. Excess substrate pNPP solution was washed away and a standard solution of BCIP/NBT was allowed to react with the specimens for ten minutes. Excess solution was washed away and each sample was analyzed by light microscopy to determine the location of Gfap protein concentration.

As seen in FIGS. 4a–4d from a patient with Alzheimer's disease, either of the antigen detection systems is capable of localizing the antigens for visual detection and both antigens are easily distinguished on the same sample. Blue PHF/tau positive neurons can be seen in panel A and brown Gfap positive astrocytes can be seen in panel B when these reactions are performed individually. When the two reactions are performed sequentially as in panels C and D, the two reactivities can be easily distinguished. Quantitative analysis with the two probe systems was also comparable. Non-Alzheimer's disease sections were easily distinguishable quantitatively from those sections which were derived from Alzheimer's diseased patients due to the difference in PHF/tau reactivity (Table 3). Also note that there was little effect of prior PHF/tau quantitation on Gfap reactivity. In a similar study using PHF/tau and WGA probes, the ratio of PHF/tau to WGA reactivity was 0.58 and 1.48 in two patients with Alzheimer's disease and less than 0.04 in each of four patients without Alzheimer's disease. The use of WGA as a probe, which binds to cell surface carbohydrates and is directly proportional to tissue volume (as in Example 1), allows a comparison of PHF/tau probe binding between samples of varying sizes.

TABLE 3

| Sample | PHF/tau $OD_{405}$ | Gfap $OD_{405}$ Pre-PHF | Gfap $OD_{405}$ Post-PHF |
| --- | --- | --- | --- |
| Alzheimer's Diseased #1 | 1.353 | 0.231 | 0.171 |
| Alzheimer's Diseased #2 | 1.638 | 0.852 | 0.651 |
| Control #1 | 0.121 | 0.271 | 0.212 |
| Control #2 | 0.008 | 0.538 | 0.536 |
| Control #3 | 0 | 1.051 | 0.899 |

EXAMPLE 6

This example illustrates quantitation and localization of antinuclear autoantibody (ANA) from serum obtained from patients.

Different patterns of nuclear labeling which are produced by ANA in patient serum are described as being homogeneous (diffuse), speckled, rim, centromere, or nucleolar and are clinically associated with particular diseases. Serial dilutions of serum from two ANA positive patients and a positive and negative control were tested to observe different patterns of antibody binding to cells and to measure the quantitative amount of ANA in the same samples.

HEp-2 human carcinoma cells (Kallestad Laboratories) served as substrate for the ANA test. Cell samples were blocked in PBS-BB and then reacted with patient serum samples diluted into PBS-BB for one hour. Cell samples were then washed three times with PBS, incubated with polyclonal horseradish peroxidase conjugated anti-human IgG (Jackson ImmunoResearch Laboratories) diluted into PBS-BB for one hour, and then washed again three times with PBS. 60 µl of a standard OPD solution (0.4 mg/ml in 0.05M phosphate citrate, pH 5.0, plus 0.4 mg/ml urea hydrogen peroxide) was added to each cell sample and reacted for a total of fifteen minutes. The OPD solution was removed and combined with 15µl of 3N HCl to terminate the enzyme-substrate reaction. Each removed solution sample was quantitated by measuring absorbance at 492 nm. The cell samples were washed three times with PBS to remove excess substrate solution and a standard DAB/metal solution was added for five minutes. The DAB/metal solution was rinsed with three washes in PBS, coverslipped with PBS:glycerol (1:1) and each cell sample was observed with a light microscope.

Figure 5A:
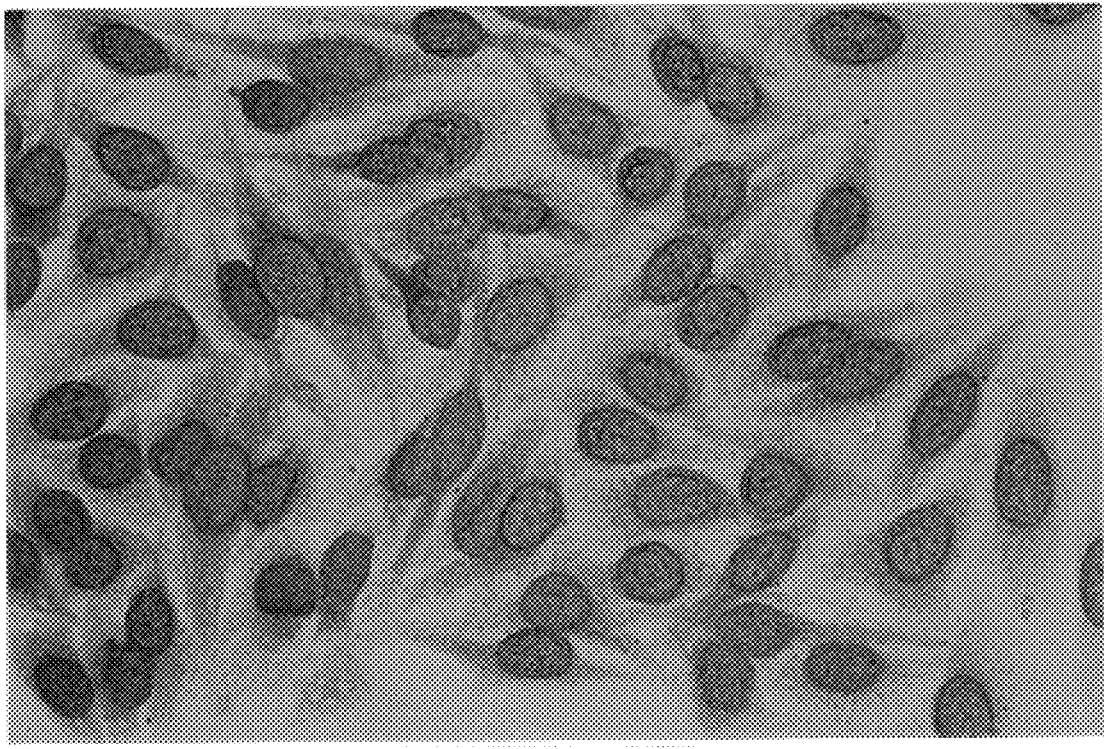
FIGS. 5A, 5B, 5C and 5D illustrates immunohistochemical staining patterns observed on slides of HEp-2 cell specimens reacted with serum samples showing (A) a diffuse pattern, (B) a speckled pattern, (C) a rim pattern, and (D) no apparent staining.
Figure 5B:
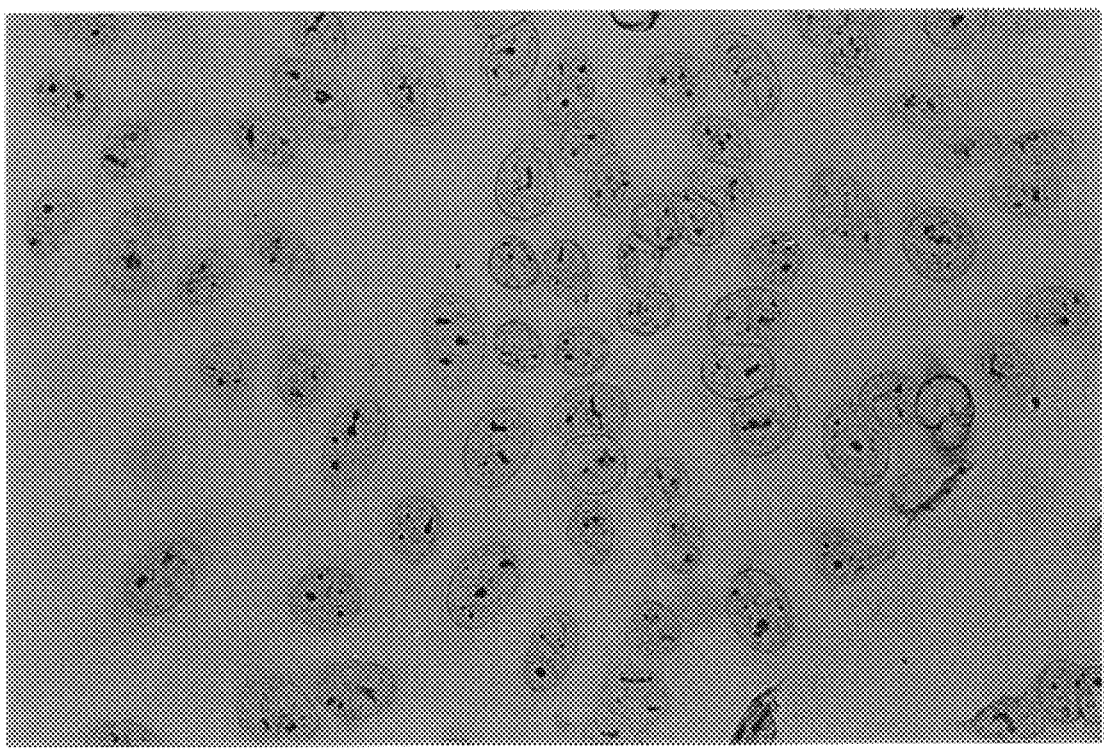
Figure 5C:
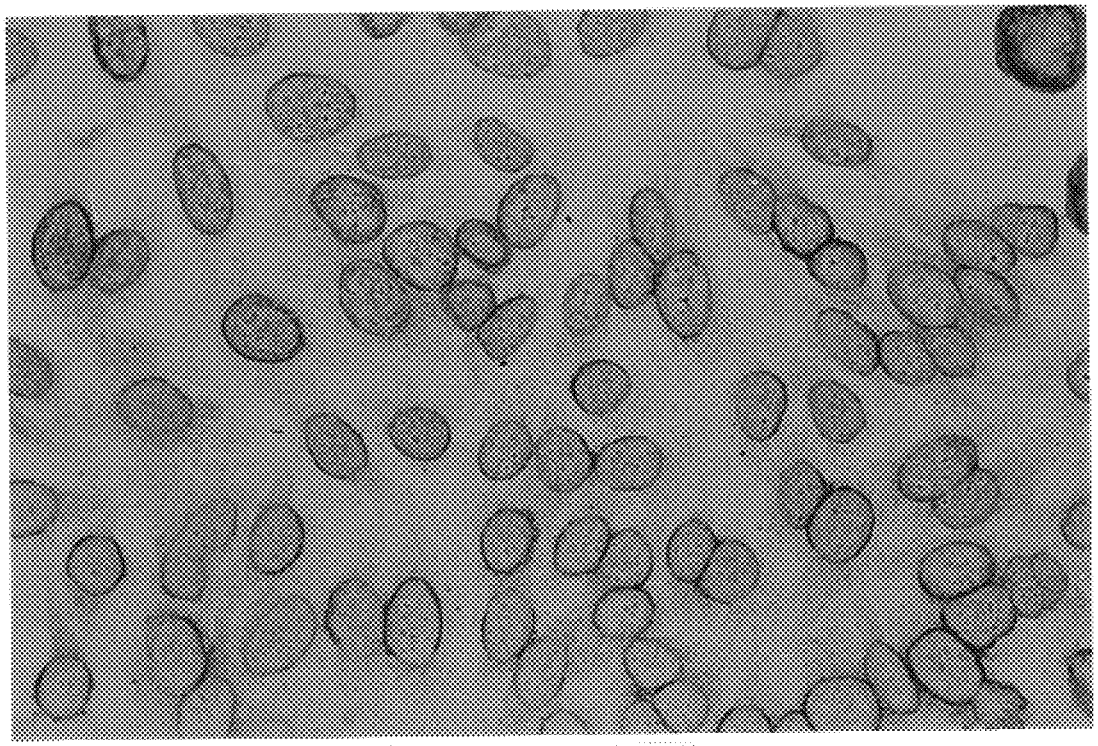
Figure 5D:
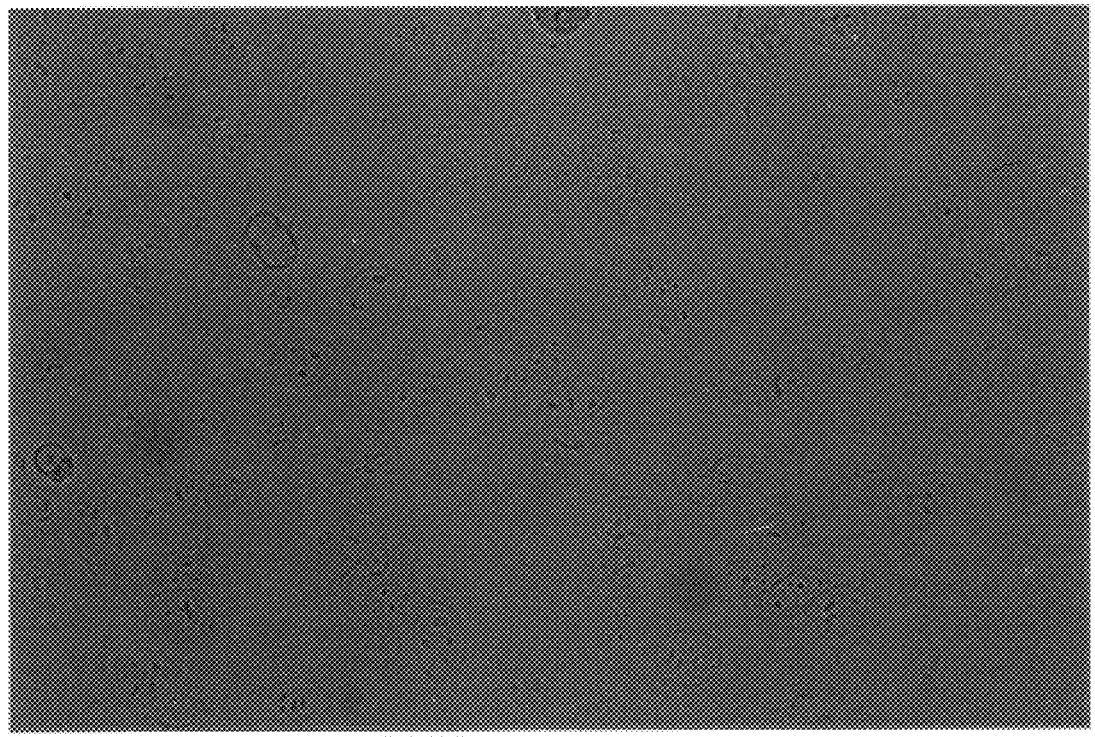

The patterns of immunohistochemical staining produced by the separate serum samples were distinctly different. The positive control showed a diffuse nuclear staining pattern which is suggestive of autoantibodies to native DNA, histones, or deoxyribonucleoprotein (FIG. 5a). A pattern of small speckles is observed within the nucleus of cells reacted with serum sample 1, which suggests the presence of autoantibodies to nuclear ribonucleoprotein (FIG. 5b). The chromogen deposited on cells reacted with serum sample 2 was predominantly at the rim or circumference or boundary of each cell nucleus which is a pattern consistent with autoantibodies against double stranded DNA (FIG. 5c). The negative control showed no apparent chromogenic deposit (FIG. 5d).

In the quantitative analysis of the cells, the positive control cell specimen, which had a diffuse chromogen deposit, produced the greatest amount of solution phase chromogen (Table 4). The serum sample 2 cell specimen which produced a rim pattern and faintly diffuse pattern produced almost as much solution phase chromogen as the positive control (Table 4).

TABLE 4

| Sample | $OD_{492}$ |
| --- | --- |
| Positive Control[1] | 0.920 |
| Negative Control[2] | 0.089 |
| Sample 1 Dilution[3] | |
| 1:40 | 0.358 |
| 1:400 | 0.215 |
| 1:4,000 | 0.157 |
| 1:40,000 | 0.082 |
| Sample 2 Dilution[2] | |
| 1:40 | 0.864 |
| 1:400 | 0.632 |
| 1:4,000 | 0.593 |
| 1:40,000 | 0.309 |

[1]Tissue shown in FIG. 5ATissue shown in FIG. 5DTissue shown in FIG. 5C However, the serum sample 1 cell specimen produced a much lower amount of solution phase chromogen, consistent with the lower titer of antinuclear antibodies known to exist in this patients' serum as determined by classical antinuclear antibody fluorescent detection methods. Thus, both the pattern of ANA distribution within the cell as well as the quantitative amount of ANA can be determined on each of the samples.

EXAMPLE 7

This example compares the ability of three different chromogenic substrates to simultaneously quantitate and localize probe binding to a target substance.

Three solutions, each containing a different chromogenic substrate dissolved in an HRP substrate buffer (0.1M Tris pH 7.5, 0.03% $H_2O_2$), were tested for their ability to simultaneously produce a solution phase product for quantitation and a solid phase deposited product for localization of a target substance in a single sample. The three chromogenic substrates tested were o-phenylene diamine dihydrochloride (OPD; 0.4 mg/ml), a commonly used HRP substrate for producing solution phase chromogen product; p-phenylene diamine dihydrochloride/pyrocatechol crystals (pPD/PC; 0.4 mg/ml pPD, 8 mg/ml PC; Fluka), a chromogenic substrate previously described for producing a solid phase chromogen product (Hanker et al., Histochem. J. 9:789–792, 1977); and pPD (0.8 mg/ml), a component of the pPD/PC mixture that is chemically similar to OPD.

Paraffin embedded mouse brain tissue sections were prepared as in Example 1, and then incubated in 0.3% $H_2O_2$ for thirty minutes to destroy endogenous peroxidase activity. Sections were then blocked in PBS-BB and incubated for one hour with 100 μl of a 1:100 dilution of horseradish peroxidase conjugated wheat germ agglutinin (WGA-HRP, EY Laboratories, 1 mg/ml stock) in PBS-BB. Sections were washed once in PBS and then two times for five minutes each time with Tris buffer, then each was reacted for five minutes with 300 μl of one of the different chromogenic substrate solutions. 100 μl samples were removed and immediately analyzed at 450 nM (pPD or OPD) or 405 nm (pPD/PC) to quantitate the amount of reaction product produced from each tissue specimen. Each tissue specimen was then washed thoroughly in water and analyzed by light microscopy.

Figure 6A:
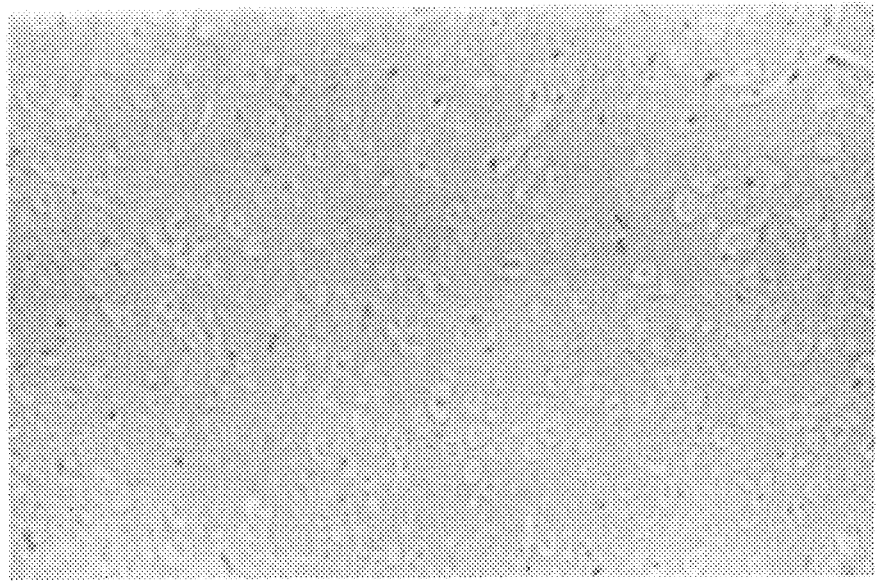
FIGS. 6A and 6B illustrates simultaneous quantitation and localization of probe binding to mouse brain tissue sections using a substrate which produces solution phase and solid phase chromogens where the enzyme substrate is (A) o-phenylene diamine dihydrochloride (OPD), or (B) a p-phenylene diamine dihydrochloride/pyrocatechol mixture (pPD/PC).
Figure 6B:
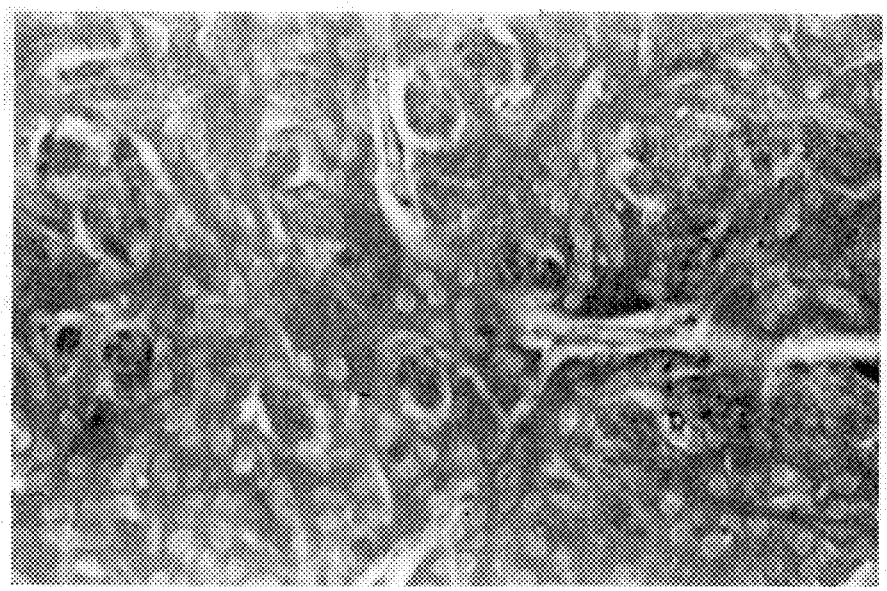

The OPD reacted sample produced predominantly a solution phase product. The OPD solution phase product measured at the absorbance maximum was determined to be 0.854 $A_{450}$. Solid phase OPD product was poorly detected (FIG. 6a). pPD produced a solution phase product which was determined to be 0.540 $A_{450}$, and a solid phase product which was more easily visualized than the OPD product (data not shown). pPD/PC provided optimal simultaneous solution phase and solid phase products. pPD/PC produced a solution phase product determined to be 0.675 $A_{405}$, and an easily visualized dark brown solid phase product at the site of probe binding (FIG. 6b). As expected for the WGA probe, a diffuse dark labeling of the neural parenchyma was observed. Thus, probe binding to a target substance can be simultaneously quantitated and localized using a single chromogen or a chromogen mixture.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method for simultaneously localizing and quantitating a target substance having a fixed location and amount in a biological sample in a bathing medium comprising:

contacting the sample with a probe which binds to the target substance wherein the bound probe is linked to an enzyme reacting the enzyme with a substrate or substrates present in the bathing medium to simultaneously produce (1) an insoluble product which deposits substantially at the target substance location and which can be detected upon illumination of the sample and (2) a soluble product which, upon illumination of the bathing medium, can be detected in an amount that is dependent upon the amount of target substance in the sample; and detecting the insoluble product in the sample and the soluble product in the bathing medium.

2. The method according to claim 1 wherein the probe is selected from the group consisting of an antibody, an avidin compound, a lectin, a receptor ligand and a nucleotide probe.

3. The method according to claim 2 wherein the probe is an antibody.

4. The method according to claim 2 wherein the enzyme is alkaline phosphatase or horseradish peroxidase.

5. The method according to claim 4 wherein the enzyme is alkaline phosphatase and the insoluble product is produced from 5-bromo-4-chloro-3-indoyl phosphate/nitroblue tetrazolium (BCIP/NBT), New Fuchsin, Fast Blue/Napthol or Fast Red/Napthol; and the soluble product is produced from Fast Red/Napthol or p-nitrophenyl phosphate (pNPP).

6. The method according to claim 4 wherein the enzyme is horseradish peroxidase and the insoluble product is produced from o-phenylene diamine dihydrochloride (OPD), a p-phenylene diamine dihydro-chloride/pyrocatechol mixture (pPD/PC), amino ethylcarbazole, chloro-napthol, diaminiobenzidine tetrachloride, or a diaminobenzidine tetrachloride/cobalt chloride and nickel chloride (DAB/metal) mixture; and the soluble product is produced from OPD, pPD/PC or tetramethyl benzidine dihydrochloride (TMB).

7. The method according to claim 6 wherein both the insoluble and soluble products are produced from pPD/PC.

* * * * *